United States Patent
Campbell

(10) Patent No.: US 6,592,568 B2
(45) Date of Patent: Jul. 15, 2003

(54) BALLOON ASSEMBLY FOR STENT DELIVERY CATHETER

(75) Inventor: Andrew J. Campbell, Reading, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 162 days.

(21) Appl. No.: 09/758,582

(22) Filed: Jan. 11, 2001

(65) Prior Publication Data

US 2002/0091435 A1 Jul. 11, 2002

(51) Int. Cl.$^7$ .............................................. A61M 31/00
(52) U.S. Cl. ........................ 604/509; 604/507; 604/508; 604/509; 623/1.11; 606/159
(58) Field of Search ................................. 604/507, 508, 604/509, 96; 514/530; 606/159

(56) References Cited

U.S. PATENT DOCUMENTS

| | | | |
|---|---|---|---|
| 5,358,487 A | * 10/1994 | Miller | ................... 604/101.02 |
| 5,366,472 A | 11/1994 | Hillstead | ................... 606/194 |
| 5,409,495 A | 4/1995 | Osborn | |
| 5,470,313 A | 11/1995 | Crocker et al. | |
| 5,645,560 A | 7/1997 | Crocker et al. | |
| 5,843,116 A | 12/1998 | Crocker et al. | |
| 5,890,531 A | 4/1999 | Gairns et al. | |
| 5,900,433 A | * 5/1999 | Igo et al. | ................... 128/898 |
| 6,027,517 A | 2/2000 | Crocker et al. | |
| 6,048,350 A | 4/2000 | Vrba | |
| 6,120,523 A | 9/2000 | Crocker et al. | |
| 6,136,011 A | * 10/2000 | Stambaugh | ............ 604/101.02 |
| 6,200,325 B1 | 4/2001 | Durcan et al. | |
| 6,290,485 B1 | 9/2001 | Wang | |
| 6,293,924 B1 | 9/2001 | Bagaoisan et al. | |
| 6,296,660 B1 | 10/2001 | Roberts et al. | |

* cited by examiner

Primary Examiner—David J. Isabella
Assistant Examiner—Kamrin Landrem
(74) Attorney, Agent, or Firm—Crompton, Seager & Tufte, LLC

(57) ABSTRACT

The present invention discloses a stent delivery catheter that reduces stent displacement during deployment. In particular, the stent delivery catheter provides expansion of a stent that originates initially from within the stent's center or medial region, that later proceeds outwardly toward the stent's ends. Medial expansion of a stent is disclosed using a multi-chambered expandable balloon or a wire member that radially expands when tubular members of the catheter shaft are longitudinally displaced.

15 Claims, 2 Drawing Sheets

BALLOON ASSEMBLY FOR STENT DELIVERY CATHETER

TECHNICAL FIELD

The present invention relates generally to the field of intravascular medical devices for stent delivery. More specifically, the present invention relates to an intravascular stent delivery catheter that provides medial balloon inflation for deterring longitudinal displacement of a stent during deployment.

BACKGROUND OF THE INVENTION

Balloon dilation catheters have been, and continue to be, a popular means of stent delivery. Current balloon catheters, however, are prone to difficulties when attempting to accurately deploy the stent across a stenosed lesion. Accurate deployment of the stent is important to the clinician, as he or she wants to place the stent directly on the diseased tissue of the vessel. Should the stent migrate to either side of the diseased tissue, some of the diseased tissue may be left untreated. In addition, healthy tissue may be adversely affected by the inaccuracy of the stent deployment procedure.

Stent misplacements occur because of specific inflation dynamics experienced by the expandable balloon when deploying the stent. Currently existing stent delivery catheters inflate the balloon portion of the catheter preferentially from either the distal or proximal end of the balloon. During inflation, the expanding balloon may form an inflation "wave" that may be said to drive or "plow" the stent so that it opens progressively from one end to the other along the front of the inflation wave. This form of balloon inflation is referred to as "end-to end" preferential inflation. End-to-end balloon inflation causes a deploying stent to displace longitudinally away from its intended delivery site, thereby potentially ineffectively treating the diseased lesion within the patient's vasculature.

In addition to end-to end preferential inflation, preferential balloon inflation may also arise from the initial inflation of the proximal and distal ends of the balloon, wherein the inflation from both ends progresses medially. This form of preferential balloon inflation is referred to as "dog boning." In some cases, such as with rigid stents, this balloon inflation dynamic may be a preferred means of limiting stent migration. With more flexible stents, however, the dog bone balloon inflation dynamic may cause the ends of the stent to shorten with respect to one another. As the proximal end and the distal end of the stent are expanded, the ends are driven toward one another. In effect, the length of the stent is forced to compress due to this particular balloon inflation dynamic.

For many applications, it is desirable to have a stent delivery catheter comprising an inflation balloon that inflates evenly. For other applications, it would additionally be desirable to provide a stent delivery catheter having a balloon that incorporates preferential inflation of a beneficial type, such as initial medial inflation.

SUMMARY OF THE INVENTION

While inadvertent preferential expansion is to be avoided, some controlled preferential balloon inflations are actually desired. With initial medial inflation, for example, the expandable balloon inflates initially at its center, with inflation then progressing simultaneously towards both ends of the balloon. The center of the balloon is initially maximally inflated, causing the center of the expanding stent to impinge upon the center of the treatable lesion or stenosis. This initial medial impingement greatly reduces longitudinal displacement of the stent during its further expansion. The balloon and stent are then allowed to expand evenly toward their respective ends resulting in securing of the stent over its length in the diseased vessel.

Medial balloon inflation is difficult to predict and achieve with currently available expandable balloons. The physics behind fluid dynamics dictates that fluid will always take the path of least resistance when filling open space. Thus, a balloon will inflate where the fluid or inflation media gathers first. From this point, a bolus of fluid will move tangentially across the balloon filling it as it moves. This inflation phenomenon is synonymous with the end-to-end balloon inflation dynamic. Similarly, two boluses of fluid may aggregate at the confining ends of the balloon and fill medially. This inflation phenomenon is synonymous with the dog bone balloon inflation dynamic.

The present invention provides a balloon where the inflation dynamics are optimized (preferably from the center outward), thereby providing for the homogeneous expansion of both the expandable balloon and stent. In an alternate embodiment of the present invention, an expandable balloon is provided that incorporates a plurality of inflatable members that may be individually controlled to achieve predictable medial balloon inflation.

To prevent dog-bone type or end-to-end preferential inflation, and provide instead either no preferential inflation or, in an alternate embodiment, medial inflation, the present invention provides a means for directing and restraining entering inflation fluid within the distensible balloon. In a representative embodiment of the invention, a medially positioned inflation member captures an initial bolus of inflation fluid entering the balloon. This inflation member serves as a dam to gather a bolus of inflation fluid while creating a space for the fluid to fill. In one embodiment, this inflation member is rupturable. Once the member bursts, the unrestrained inflation fluid is released into the remaining portions of the expandable balloon. The expandable balloon is then further inflated to expand the remaining portions of both the balloon and stent.

In an alternative embodiment of the present invention, the inflation member does not rupture. The inflation member of this embodiment is comprised of a semi-permeable material. The material forming the inflation member selectively leaks at sufficiently high pressures. Thus, the bolus of fluid restrained within the inflation member slowly leaches from the inflation member, thereby expanding the remaining portions of both the balloon and stent.

In another embodiment of the present invention, a wire member is disposed over the distal end of the stent delivery catheter. The wire member expands and contracts with the longitudinal displacement of tubular members within the catheter's shaft. With the appropriate displacement of the tubular members, the wire member first medially expands, impinging the center of a loaded stent against the diseased lesion. In particular embodiments, an expandable balloon may be disposed over the wire member. The expandable balloon may then be inflated to further expand the remaining portions of both the balloon and stent.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DETAILED DESCRIPTION OF THE PREFERRED EMBODIMENTS

The following detailed description should be read with reference to the drawings, in which like elements in different drawings are numbered identically. The drawings, which are not necessarily to scale, depict selected embodiments and are not intended to limit the scope of the invention. Examples of construction, materials, dimensions, and manufacturing processes are provided for selected elements. All other elements employ that which is known to those skilled in the field of the invention. Those skilled in the art will recognize that many of the examples provided have suitable alternatives that may be utilized.

Figure 1:
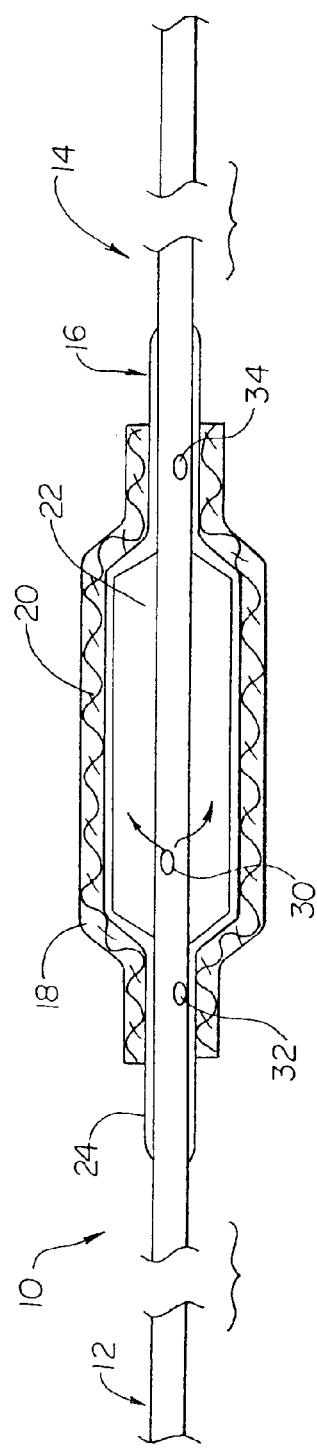
FIG. 1 is a partial cross-sectional view of a stent delivery catheter of the present invention having a balloon region where one inflation member, within a deflated second inflation member, is inflated.

FIG. 1 shows a partial cross-sectional view of a stent delivery catheter 10 in accordance with the present invention. In particular, FIG. 1 shows a stent delivery catheter 10 that includes a catheter shaft 12 having a proximal end (not shown) and a distal end 14. A plurality of lumens extend within the catheter shaft 12. The various lumens connect features of the catheter 10 to a source located at the proximal end of the catheter. Examples of lumens extending within catheter 10 include a guidewire lumen and at least one inflation lumen. In preferred embodiments of the present invention, two or three inflation lumens extend along a portion of the catheter shaft 12. Connection of a lumen with its corresponding source is generally accomplished using a manifold positioned on the proximal-most end of the catheter 10. Inflation ports on the manifold fluidly connect and direct ancillary devices to their corresponding lumens. The inflation ports possesses a luer lock fitting on the proximal end of the inflation port that mates with a corresponding connector on the appropriate ancillary device.

At the distal-most end of catheter 10 is a distal tip that aids the catheter in navigation through the tortuous vasculature of the patient. Modifications in the shape and size of the distal tip further aid the catheter in crossing stenosed lesions within the vasculature. Proximal the distal-most end of catheter 10 is an expandable dilation balloon 16. Expandable balloon 16 carries an expandable stent 18 that is loaded over the balloon. Expandable stent 18 of the present invention is shown as a wire-like member comprising a plurality of interconnected strut-like members 20. Strut-like members 20 are fabricated in defined patterns to provide radial expansion. The wire-like stent 18 expands radially when a pressure is exerted within the inner walls of the stent. Although a wire-like stent is specifically depicted, the use of other expandable stents 18 for intravascular purposes is possible without deviating from the spirit and scope of the present invention.

The expandable stent 18 is loaded over the balloon 16 in a constricted or compacted state. The manufacturer generally loads stent 18; however, a member of the surgical, radiology or cardiology staff may additionally load stent 18 within a clinical environment. When discussing the relative positioning of stent 18, a "compacted configuration" is when stent 18 is crimped upon the catheter 10 so that the stent's profile closely mimics the profile of the catheter shaft 12. An "expanded configuration" is when stent 18 has been radially expanded by inflation of the expandable balloon 16. It is within the scope of the present invention to have a stent configuration where a portion of the stent is within the compacted configuration, whereas another portion is expanded.

Expandable balloon 16 includes two inflatable members, an inner inflation member 22 and an outer inflation member 24. Both the inner 22 and outer 24 inflation members are attached to the catheter shaft 12. Laser, adhesive, hot melt and thermal bonding are all acceptable methods for adhering the inflation members 22 and 24 to the catheter shaft 12. As their names denote, however, the inner inflation member 22 is positioned under the outer inflation member 24. The inner inflation member 22, therefore, is adhered to a portion of the shaft 12 within the area defined by the outer inflation member 24. Only outer tubular member 24 is in physical contact with the expandable stent 18. The outer wall of the inner inflation member 22 contacts the inner wall of the outer inflation member 24.

Inner inflation member 22 is generally shorter in length and inflated height than the outer inflation member 24. In alternate embodiments, the inner inflation member 22 has an inflated height equivalent to the inflated height outer inflation member 24. The length of the inner inflation member 22 is centered, with respect to the length of the outer tubular member 24, within the outer inflation member 24. The inner inflation member 22 is preferably stretched longitudinally during its mounting and subsequent adherence to the catheter shaft 12. Stretching the inner inflation member thins the polymeric material, allowing the inner inflation member 22 to burst under pressure when desired, as discussed in detail below.

Material selection for inner inflation member 22 includes those materials having desired expansion and burst pressures. The inner inflation member 22, therefore, is generally composed of a highly flexible and distensible material. Materials suitable for inner inflation member 22 include highly flexible polymeric materials. In preferred embodiments, the inner inflation member 22 is comprised of latex, a polyolefin such as ethylene vinyl acetate (EVA), as well as other suitable thermoplastic elastomers.

In a representative embodiment, the inner inflation member 22 may possess a line of weakness (not shown). A line of weakness includes a perforation or scoring of the material forming the inner inflation member 22. In preferred embodiments, scoring of the inner inflation member 22 material is made circumferentially about the inflation member. Circumferential scoring allows the inner inflation member 22 to split radially. Under sufficient pressure, a radial split will cause the perforated inner inflation member 22 to "snap back" away from the center of the inflation member. In alternative embodiments, the inner inflation member 22 may be scored longitudinally, or at the inflation member's ends. The depth of the scoring must provide a balance between sufficient inflation strength and predictable bursting pressures. In one embodiment, an instrument scoring the inner inflation member 22 at a depth that closely approximates one-third of the inflation member's total wall thickness is proven to provide sufficient inflation and bursting predictability.

In an alternative embodiment, the inner inflation member 22 is semi-permeable under certain inflation pressures. The walls of a semi-permeable inner inflation member 22 may be porous. For example, the sizes of the pores found within the walls of the member dilate with the inflation of the inner inflation member 22. The pores within the walls are too small to permit significant fluid from escaping under little or no inflation pressure. Under sufficiently high inflation pressures, however, inflation fluid may escape through the dilated pores into the surrounding volume (defined under the outer inflation member 24).

The outer inflation member 24 comprises a less flexible and less distensible material than the inner inflation member 22. Materials suitable for the outer inflation member 24 include generally noncompliant polymeric materials. In preferred embodiments, the outer inflation member 24 is comprised of polyether block amide (PEBA), polyethylene, polyethylene terephthalate (PET), as well as other suitable thermoplastic polymers. The outer inflation member 24 can also comprise semi-compliant polyamides, polyether block amides or nylons, as well as hinged compliant materials such as polybutylene terephthalate (PBT) and Arnitel.

A series of lumen openings 30,32,34 are depicted along the length of the catheter shaft. The number of lumen openings depicted is for illustrative purposes only. The number of lumen openings may vary depending upon the catheter used and the desired application for the catheter. The lumen openings in FIG. 1 are shown to illustrate possible opening placements and the resulting effects of such placements.

A first lumen opening 30 is positioned under inner inflation member 22 only. Two additional lumen openings, 32 and 34, are positioned only under the outer inflation member 24. Lumen openings along catheter shaft 12 may share a common inflation lumen, or the openings may correspond to individual inflation lumens extending within the catheter shaft 12. Multiple inflation lumens permit an operator to vary fluid pressures experienced at different regions within the expandable balloon 16. For example, assuming the two lumen openings 32 and 34 under the outer inflation member 24 are connected, while separate from the lumen opening 30, an operator may increase the fluid pressure within inner inflation member 22 while at the same time reducing the fluid pressure within outer inflation member 24. This regulation is all done by controlling the inflation fluid flow rates entering and exiting the corresponding lumen openings.

Stent movement during deployment is reduced when the stent 18 is first expanded medially. Medial balloon inflation causes the center of stent 18 to expand first. This initial expansion impinges the center of stent 18 against the surrounding vessel wall and reduces longitudinal displacement during further expansion of the balloon 16 and stent 18. Additionally, homogeneous expansion of the stent 18 also reduces longitudinal displacement. The expandable balloon 16 of the present invention provides for either medial or homogeneous expansion of the expandable stent 18 by selectively controlling the inflation fluid pressure and rate of inflation within the various portions of the balloon.

Medial expansion of stent 18 occurs through initial inflation within the center of the expandable balloon 16. In preferred embodiments, the inner inflation member 22 has at least one dedicated inflation lumen feeding the member. An operator of the stent of the present invention, therefore, may inflate only the center of the expandable balloon 16 when desired. The operator feeds inflation fluid through the appropriate inflation lumen into the inner inflation member 22.

The inner inflation member 22 then expands, having the uninflated outer inflation member 24 draped over the inner inflation member's profile. The center of the stent 18 additionally expands roughly following the profile of the inner inflation member 22, as seen in FIG. 1. The inner inflation member 22 is generally expanded until stent 18 engages the surrounding vessel wall. Impinging stent 18 against the vessel wall greatly reduces the possibility of stent displacement along the vessel's longitudinal axis.

In certain embodiments, sufficient inflation pressures within the inner inflation member 22 may cause the inner inflation member to burst. Bursting pressures generally occur after the inner inflation member 22 can no longer radially inflate (e.g., after the inner inflation member 22 has set stent 18 against the surrounding vessel wall). Confining the expansion of balloon 16 increases internal balloon pressure. The highly flexible and distensible material of the inner inflation member 22 is finally stressed to a bursting point where the member ruptures.

Rupturing of the inner inflation member 22 allows inflation fluid from within the inner inflation member 22 to disperse into the outer inflation member 24. Additional inflation fluid is then supplied to the outer inflation member 24 to further expand the unexpanded portions of stent 18. The additional inflation fluid may continue to be supplied through lumen opening 30, dedicated to the inner inflation lumen, or additional inflation lumens may be used that have lumen openings 32 and 34 dedicated only within the outer inflation member 24. The outer inflation lumen 24 is then radially expanded to impinge the remaining portions of stent 18 against the vessel wall.

An inner inflation member 22 capable of bursting under controlled circumstances is also useful in drug delivery applications. Therapeutic drugs that treat stenotic lesions often require mixing at the point of delivery. Few methods exist for mixing solutions deep within the vasculature of a patient. The combination of a rupturable inner inflation member 22 with a porous outer inflation member 24 creates an effective device for therapeutic drug treatment.

In operation, one therapeutic drug may be used to inflate the inner inflation member 22 while a second therapeutic drug is used to partially inflate the outer tubular member 24. When the highly flexible and distensible material of the inner inflation member 22 ruptures, the bolus of drugs held in the inner inflation member 22 disperses into the outer inflation member 24. The rupturing of the inner inflation member 22 causes the two therapeutic drugs to thoroughly mix. Increasing the inflation pressure within the outer inflation member 24 allows the mixed therapeutic drugs to disperse out of the outer inflation member 24, and onto the lesion.

As described above, the bursting pressure and/or direction of rupturing experienced by the inner inflation member 22 may be controlled through preferential scoring or perforation of the member wall. Circumferential scoring of the vessel wall is particularly useful when the lumen opening 30 is centrally positioned under the inner inflation member 22. The combination of proper lumen opening placement and circumferential scoring helps ensure that lumen opening 30 remains patent after rupturing. Because the circumferential scoring forces a radial split of the inflation member 22, the resulting "snap back" of the remaining member material away from the center of the inflation member reduces the chance that the balloon will cover the centrally located lumen opening 30. Maintaining patency of lumen opening 30 is particularly important for deflation purposes. Catheter 10 must be withdrawn from the patient's vasculature after treatment. In order to withdraw catheter 10, balloon 16 must first be deflated. The combination of central lumen opening placement and circumferential scoring is believed to enhance the deflation procedure.

In alternative embodiments having multiple inflation ports and/or lumens, another lumen opening may be used to deflate the expanded balloon. Specifically to FIGS. 1 and 2, lumen openings 32 and 34, positioned only under outer inflation member 24, can be used to deflate the outer inflation member 24 following completion of the medical procedure.

Operating multiple inflation lumens that terminate distally within an expandable balloon 16 requires a certain degree of skill. Lumens that are not active in the process of pressurization or deflation of the expandable balloon 16 need to be sealed off. Failure to seal dormant inflation lumens may prevent the expandable balloon 16 from reaching operational inflation pressures. While one inflation lumen is inflating the balloon, another unsealed inflation lumen may be deflating the balloon. The use of additional apparatus to plug dormant inflation lumens during critical inflation and deflation procedures may ensure proper pressurization of expandable balloon 16.

In a preferred embodiment, a solid rod plug is inserted within a portion of a dormant inflation lumen. The solid rod plug comprises a flexible shaft having a proximal end, a distal end and a length that closely approximates the length of the inflation lumen. Shorter length plugs may also be used. The outer diameter of the plug's flexible shaft sealably slides within the inner diameter of the dormant inflation lumen. The proximal end of the plug generally possesses a luer lock fitting. This luer lock fitting mates and seals with a corresponding luer connector on the inflation port of the catheter manifold. In operation, the distal end of the plug is advanced through the dormant inflation lumen until the proximal end of the plug connects with the inflation port connector. The plug is then sealably connected to the manifold, thereby preventing inflation fluid from escaping through the dormant lumen. When the dormant inflation lumen is to be utilized, the plug may be withdrawn from the lumen, thereby allowing the lumen to be operational for inflation or deflation of expandable balloon 16.

In an alternative embodiment, a hollow rod may be inserted within the dormant inflation lumen. The hollow rod has a proximal end, a distal end and a flexible lumen shaft extending the length therethrough. The outer diameter of the flexible hollow rod sealably slides within the inner diameter of the dormant inflation lumen. The flexible hollow rod generally extends the length of the inflation lumen. At the proximal end of the hollow rod are matching openings that correspond with the inflation lumen openings, for example 30, 32 and 34, which fluidly connect expandable balloon 16 with the inflation lumen. In a first position, the openings within the hollow rod synchronize with the inflation lumen openings. This position allows the hollow rod to be in fluid communication with the expandable balloon 16. When the shaft of the hollow rod is rotated, however, the openings no longer match. The lumen wall of the hollow rod sealably obstructs the inflation lumen openings. The expandable balloon 16 lacks fluid communication with either the hollow rod or the inflation lumen when the hollow rod is rotated into this configuration. Therefore, the openings of the hollow rod must align properly with the inflation lumen openings in order to utilize an inflation lumen having the hollow rod inserted therein.

Figure 2:
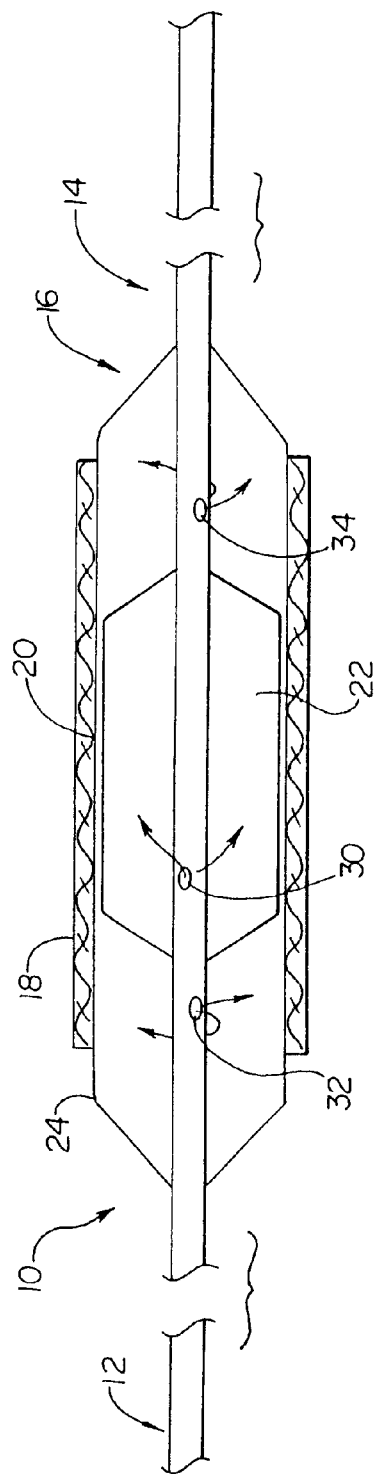
FIG. 2 is a partial cross-sectional view of the stent delivery catheter of FIG. 1, wherein the first and second inflation members are both inflated.

Medial expansion of a stent 18 may be provided using additional embodiments. In one such embodiment, the inner inflation member 22 comprises a semi-permeable, porous wall material, as described above. As with previous embodiments, an inflation fluid is supplied only to the inner inflation member 22. Inner inflation member 22 inflates radially, resulting in the medial impingement of stent 18 against the treated vascular wall. The inner inflation member 22 continues to expand until the internal pressure within the member causes inflation fluid to escape through the member's wall. A constant stream of inflation fluid, directed only within inner inflation member 22, eventually inflates the outer inflation member 24. To expedite the process, additional inflation fluid may be supplied through lumen openings 32 and 34, dedicated to the inflation of outer inflation member 24. FIG. 2 shows inflation fluid filling both the inner 22 and outer 24 inflation members concurrently. With or without the additional inflation fluid, the outer inflation member 24 eventually expands to impinge the remaining portions of stent 18 against the treated vascular wall.

In yet another embodiment, additionally depicted by FIG. 2, inflation fluid is supplied to both the inner inflation member 22 and the outer inflation member 24 concurrently. Different from prior embodiments, however, all regions of the expandable balloon 16 are inflated concurrently, resulting in the homogenous radial expansion of stent 18. Incorporating a dedicated inflation lumen and inflation member within the center of expandable balloon 16 ensures proper medial inflation. Providing dedicated inflation lumen openings 32 and 34 within the remaining sections of balloon 16 similarly controls inflation within those regions. More specifically to FIG. 2, lumen openings 32 and 34 at the ends of expandable balloon 16 either can share or be individually connected to inflation lumens in order to ensure proper fluid distribution within the balloon.

Homogeneous radial expansion of stent 18 occurs when an operator inflates the outer inflation member 24 concurrently with the inner inflation member 22. Controlling the inflation rates within the expandable balloon 16 causes stent 18 to expand radially in a homogeneous fashion. The stent 18, therefore, uniformly impinges upon the treated vessel. Uniform impingement greatly reduces the possibility of stent 18 displacing along the vessel's longitudinal axis during deployment.

Figure 3:
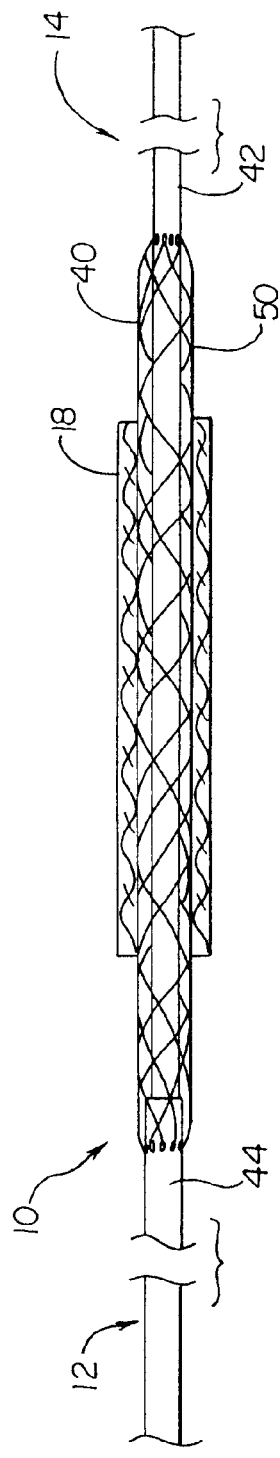
FIG. 3 is a partial plan view of a stent delivery catheter of the present invention, having an expandable wire member region disposed under a stent.

FIG. 3 shows a stent delivery catheter 10 having an expandable wire member 40. In particular, FIG. 3 shows a stent delivery catheter 10 that includes a catheter shaft 12 having a proximal end (not shown) and a distal end 14. Catheter shaft 12 in FIG. 3 includes at least two tubular members, an outer tubular member 42 and an inner tubular member 44. The inner tubular member 42 extends from the proximal-most end of catheter 10 to the distal-most end of catheter 10. The outer tubular member 44 is circumferentially disposed over a portion of the inner tubular member 42. More specifically, the outer tubular member 44 extends from the proximal-most end of catheter 10 to a point proximal the distal-most end of catheter 10. The inner tubular member 42 and the outer tubular member 44 may be relatively displaced with respect to one another. In particular, inner tubular member 42 may be longitudinally displaced within the outer tubular member 44.

An expandable wire member 40 spans distally from the distal-most end of outer tubular member 44 to a distal portion of inner tubular member 42. The expandable wire member 40 includes a plurality of wire elements 50 that are woven in patterns to provide radial expansion. Materials suitable for the wire elements 50 include nitinol, stainless steel, and semi-rigid polymeric materials. One end of a wire element 50 is anchored to the outer tubular member 44, while the other end is anchored to the inner tubular member 42. In a preferred embodiment, a balloon material (not shown) is disposed over the expandable wire member 40, as with the outer inflation member of previous embodiments.

Similar to previous embodiments, an expandable stent 18 is loaded upon the expandable wire member 40. The expandable stent 18 expands radially when a pressure is exerted from within its inner walls. Although a wire stent is specifically depicted, the use of other stents for intravascular purposes is possible without deviating from the spirit and scope of the present invention.

Figure 4:
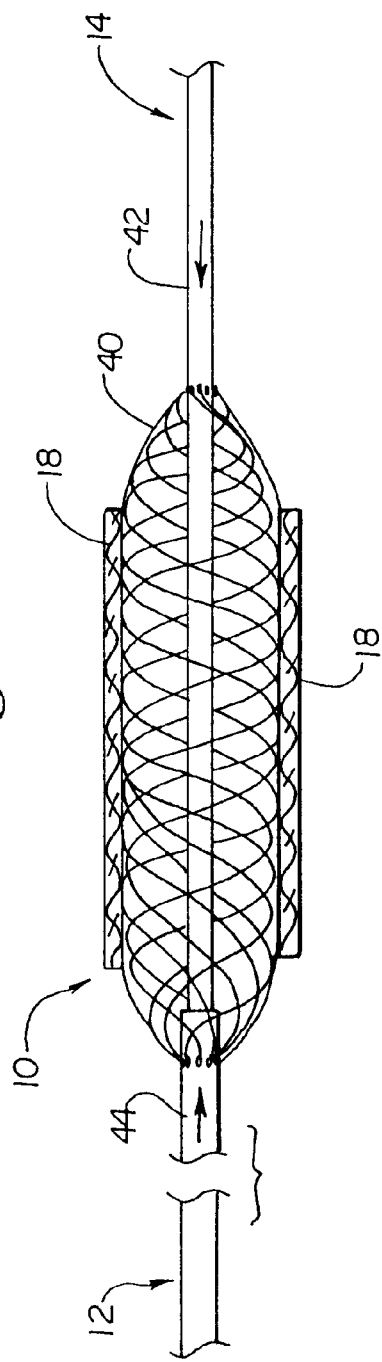
FIG. 4 is a partial plan view of the stent delivery catheter of FIG. 3, wherein the wire member expands causing the radial displacement of the stent.

Longitudinal displacement between the inner 42 and outer 44 tubular members forces wire member 40 to radially expand, as shown in FIG. 4. In preferred embodiments, wire member 40 expands first medially, and then from the center outward. Medial expansion of wire member 40 impinges the center of stent 18 into the patient's vascular wall. As with medial inflation, medial expansion of wire member 40 greatly reduces the possibility of stent displacement along the vessel's longitudinal axis. Further longitudinal displacement of the inner 42 and outer 44 tubular members of the catheter shaft permits the wire member 40 to fully expand, thereby impinging the remaining portions of stent 18 against the surrounding vessel wall.

As described above, an expandable balloon (not shown) may overlay the wire member 40 of the present invention. With certain procedures, the expandable balloon complements the expansive properties of wire member 40. More specifically, inflation of the expandable balloon, following medial expansion with wire member 40, may further set and impinge stent 18 against the surrounding vascular wall. Balloon inflation generally provides greater uniform pressure on the inner walls of a stent. This increased surface contact aids in stent deployment when particularly difficult stenosed lesions are involved.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is of course defined in the language in which the appended claims are expressed.

What is claimed is:

1. A stent delivery catheter comprising:
   a shaft having a proximal end, a distal end, a length extending therebetween, and at least one inflation lumen extending along at least a portion of the length;
   a first inflation member having a first material, the first inflation member further having a proximal end, a distal end and an expandable region therebetween, the expandable region of the first inflation member being expandable to a first diameter;
   a second inflation member having a second material, the second inflation member further having a proximal end, a distal end and an expandable region therebetween coaxially disposed within the first inflation member, the expandable region of the second inflation member being expandable to a second diameter;
   a stent disposed over the first inflation member;
   wherein the second inflation member includes a line of weakness over a portion thereof; and
   wherein the line of weakness is a scoring.

2. The stent delivery catheter of claim 1, wherein the second inflation member is substantially centered within the first inflation member.

3. The stent delivery catheter of claim 1, wherein the second material of the second inflation member is selected from the group consisting of latex, polyolefin, polyethylene, or combinations thereof.

4. The stent delivery catheter of claim 1, wherein the line of weakness is a perforation.

5. The stent delivery catheter of claim 1, wherein expansion of the second inflation member beyond the second diameter causes an integrity failure in the second inflation member.

6. The stent delivery catheter of claim 1, wherein the second inflation member is semi-permeable.

7. The stent delivery catheter of claim 1, wherein the first inflation member is semi-permeable.

8. The stent delivery catheter of claim 1, wherein the first material of the first inflation member is selected from the group consisting of polyether block amide (PEBA), a polyethylene, a polyethylene terephthalate (PET), or combinations thereof.

9. The stent delivery catheter of claim 1, wherein a first inflation port through the shaft is positioned longitudinally under the second inflation member, the inflation port being in fluid communication with a first inflation lumen.

10. The stent delivery catheter of claim 9, wherein a second inflation port is positioned longitudinally under the first inflation member only, the second inflation port being in fluid communication with a second inflation lumen.

11. The stent delivery catheter of claim 10, wherein a first therapeutic agent is in fluid communication with the first inflation port.

12. The stent delivery catheter of claim 11, wherein a second therapeutic agent is in fluid communication with the second inflation port.

13. A method for initial medial inflation of a balloon in a patient's vasculature, the method comprising the steps of:
   providing a catheter having a proximal end, a distal end, and at least one inflation lumen extending through at least a portion thereof, the catheter further having a first inflation member and a second inflation member, the second inflation member disposed within the inflatable portion of the first inflation member, the first inflation member being expandable to a first diameter and the second inflation member being expandable to a second diameter;
   providing a stent disposed over the first inflation member and placing the stent at a desired location within the vasculature;
   inflating the second inflation member within the first inflation member to cause medial expansion of the stent; and
   inflating the first inflation member to cause further expansion of the stent and seat the stent over its length within the patient's vasculature;
   wherein the second inflation member ruptures through over inflation to cause inflation of the first inflation member; and
   wherein the rupturing of the second inflation member occurs through fissure along a preformed line of weakness.

14. The method of claim 13, wherein the second inflation member comprises a material selected from the group consisting of latex, a polyolefin, a polyethylene, or a combination thereof.

15. The method of claim 13, wherein the first inflation member comprises a material selected from the group consisting of polyether block amide (PEBA), polyethylene, polyethylene terephthalate (PET), or combinations thereof.

* * * * *